United States Patent [19]
Robinson

[11] Patent Number: 5,604,295
[45] Date of Patent: Feb. 18, 1997

[54] CALIBRATING PARTICLE EMISSION-DETECTING INSTRUMENTS

[75] Inventor: David P. Robinson, Dibden Purlieu, United Kingdom

[73] Assignee: British-American Tobacco Company Limited, Staines, England

[21] Appl. No.: 625,523

[22] Filed: Mar. 27, 1996

[30] Foreign Application Priority Data

Mar. 29, 1995 [GB] United Kingdom .................. 9506394

[51] Int. Cl.⁶ .................................................. G01N 17/00
[52] U.S. Cl. ................................................................ 73/1 G
[58] Field of Search .......................... 73/28.01, 1 G, 73/1 R, 3, 861.07

[56] References Cited

U.S. PATENT DOCUMENTS

| | | | |
|---|---|---|---|
| 3,491,592 | 1/1970 | Evers et al. ........................... | 73/861.07 |
| 3,679,973 | 7/1972 | Smith, Jr. et al. ...................... | 73/28.02 |
| 3,693,401 | 9/1972 | Purt et al. .............................. | 73/1 G |
| 4,167,870 | 9/1979 | Haas ..................................... | 73/861.07 |
| 4,670,137 | 6/1987 | Koseki et al. .......................... | 73/28.01 |
| 5,502,998 | 4/1996 | Miller et al. ............................ | 73/1 G |

*Primary Examiner*—Robert Raevis
*Attorney, Agent, or Firm*—Kane, Dalsimer, Sullivan, Kurucz, Levy, Eisele and Richard

[57] ABSTRACT

In the calibration of a dust concentration measuring instrument at very low dust in gas concentration levels dust is introduced at a known and uniform rate into a gas stream and the instrument is caused to provide a detected concentration value.

7 Claims, 2 Drawing Sheets

CALIBRATING PARTICLE EMISSION-DETECTING INSTRUMENTS

BACKGROUND OF THE INVENTION

1. Field of the Invention

The present invention relates to the calibration of particle emission-detecting instruments.

2. Brief Description of Related Art

In many countries regulations require that manufacturers control the amount of particulate emissions released into the environment. Emissions should be regularly monitored in order to ensure that the emissions are below the maximum levels permitted. There is a requirement that the instruments used to monitor the emissions be calibrated regularly in accordance with a standard methodology as per, for example, that of BS 3405 of the British Standards Institution.

BS 3405 is the British Standard method of measuring the concentration of particulate matter in a gas flow, e.g. emission gases in a chimney stack. The values obtained in accordance with BS 3405 are used to calibrate the instruments used to monitor particulate emissions. The method of BS 3405 involves taking a series of samples at various positions transverse of the gas flow. The series of samples is used to calculate an average mass flow rate of particulate matter through the chimney stack or other duct in question.

The sampling technique utilised in respect of BS 3405 requires the provision of isokinetic sampling equipment. The isokinetic sampling equipment should comprise sample means for isokinetically withdrawing a sample volume of the emission gas together with particulate matter associated with the sample volume. An isokinetic method of sampling ensures that the emission gas is subject to a minimum only amount of disturbance occasioned by the presence of the gas flow of the sampling means.

The measurements made according to the method of BS 3405 are claimed to be accurate only to within ±25%. Furthermore, the lower limit of instruments currently used to calibrate particulate emission monitoring instruments according to BS 3405 can well be above the lower levels of particulate emissions being monitored. Therefore, the method of BS 3405 is ineffective for calibrating instruments that monitor very low concentrations of particulate emissions.

SUMMARY OF THE INVENTION

It is an objective of the present invention to provide means, not involving isokinetic sampling, effective for calibrating instruments that monitor very low concentrations of particulate emissions.

The present invention provides a method of calibrating a particle emission-detecting instrument, wherein particulate material is introduced at a controlled rate into a gas stream flowing through a duct, and during the controlled rate introduction of said particulate material into said gas stream said instrument is caused to provide a detection value of the concentration of said particulate material within said gas stream in said duct, whereby said instrument is calibrated.

DETAILED DESCRIPTION OF THE INVENTION

Figure 1:
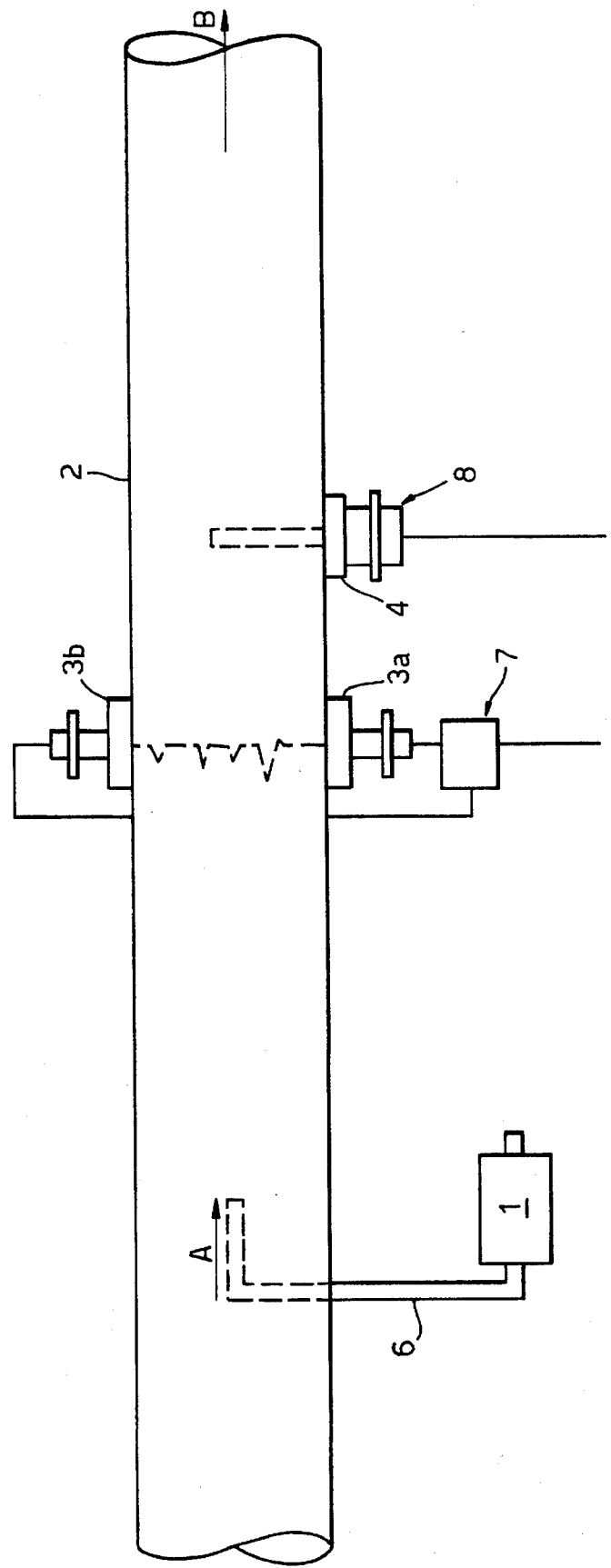

The present invention also provides a method of calibrating a particle emission-detecting instrument, wherein particulate material is introduced at a controlled rate into a gas stream flowing through a duct, the introduction being by means of a supply device, the supply device comprising a material containment chamber, material feed means, transfer means and entrainment means, said feed means being operable to feed a body of said particulate material contained in said chamber towards said transfer means at a constant rate, said transfer means being operable to transfer said particulate material from the upper surface of said body of particulate material to said entrainment means, and said entrainment means being operable to entrain said particulate material into said gas stream from said transfer means, wherein during the controlled rate introduction of said particulate material into said gas stream, said instrument is caused to provide a detection value of the concentration of said particulate material in said gas stream in said duct, whereby said instrument is calibrated.

Preferably, the said controlled rate introduction of particulate material into the duct is a uniform rate introduction. The word "uniform" as used herein is used in the sense that the degree of uniformity, of the rate of introduction of the particulate material into the gas stream, is that requisite to the calibration of the particle emission-detecting instrument to a desired degree of accuracy.

It is preferable, in order to ensure a uniform rate of introduction of the particulate material into the gas stream, for the feed means to be operable to feed the body of particulate material to the transfer means at a uniform rate and for the transfer means to be operable to transfer the particulate material to the entrainment means at a uniform rate.

Suitably the body of particulate material takes the form of a vertically extending such body.

The particulate material may take the form of a dust-like material, for example, tobacco dust or alumina dust. Such dust may have a particle size within the range of 0.1 μm to 100 μm. Furthermore, the particulate material is preferably fluid and not a tangled mass of particles.

The specific particulate material used to constitute the said body will depend upon the typical atmosphere being monitored by the instrument. In other words, the particulate material used to calibrate the particle emission-detecting instrument preferably comprises the type of particulate material monitored by the particle emission-detecting instrument, or is exemplary of such material.

The method of the present invention may be carried out effectively with a duct of any practical cross-sectional shape. Furthermore, it is not necessary to have a constant cross-section along the full length of the duct. The gas stream flowing through the duct is preferably the gas stream which flows through the duct when in normal use. The flow rate of the gas flowing through the duct can be measured accurately according to known techniques.

The material feed means preferably comprises an upwardly moveable piston an upper surface of which bounds the material containment chamber. Drive means of the material feed means may take the form of, for example, an electronic stepping motor.

The transfer means may, for example, take the form of a circular, rotary brush.

Suitably, a gas stream into which the entrainment means entrains the particulate material is provided by the entrainment means as a gas stream (of uniform flow rate) which at the entrainment location is distinct from the gas stream in the duct. In such case, downstream of the entrainment location the entrainment gas stream is directed into the duct, whereupon the particulate material entrained with the entrainment gas stream becomes dispersed in the total gas stream in the duct. Alternatively, the gas stream into which the entrainment means entrains the particulate material, instead of being a distinct gas stream at the entrainment location, is the said gas stream in the duct. In other words, the particulate material is in this case entrained directly from the transfer means into the gas stream in the duct.

The present invention further provides apparatus operable to calibrate a particle emission-detecting instrument, which apparatus comprises a supply device, a duct and mounting means, said supply device being operable to introduce, at a controlled rate, particulate material to a gas stream flowing through said duct, and said mounting means being remote said supply device longitudinally of said duct and being of a configuration requisite for the mounting of said instrument in a position for the detection of said material in said duct.

The calibration apparatus may further comprise conduit means, which conduit means serves to intercommunicate the material outlet of the supply device and the interior of the duct, whereby in operation of the supply device particulate material is fed therefrom via the said material outlet and through the conduit means to the interior of the duct. The conduit means may open at the interior of the duct at an end zone of the duct. Preferably, the conduit means opens at or in the vicinity of the centreline of the duct.

The apparatus of the present invention may comprise a duct of any practical cross-sectional shape. Furthermore, it is not necessary that the duct has a constant cross-section along the entire length. The duct may be part of a production unit; alternatively the duct may be part of an off-site test rig. Thus an instrument may be calibrated either in situ at a production unit duct or by use of a test rig.

In a case in which the gas stream is that normally flowing through a production unit duct, the gas flowing through the duct during calibration need not be filtered if the background level of particulate matter in the gas stream is not too high relative to the amount of particulate material to be introduced into the gas flow by the supply means and if the background level is sufficiently uniform. In these circumstances it is practical for the particle emission-detecting instrument to first record the background particulate material level and then, upon the particulate matter being introduced into the gas stream in the duct by the supply device, for the instrument to measure a level which is the addition of the background level and the introduced level of particulate matter.

Figure 2:
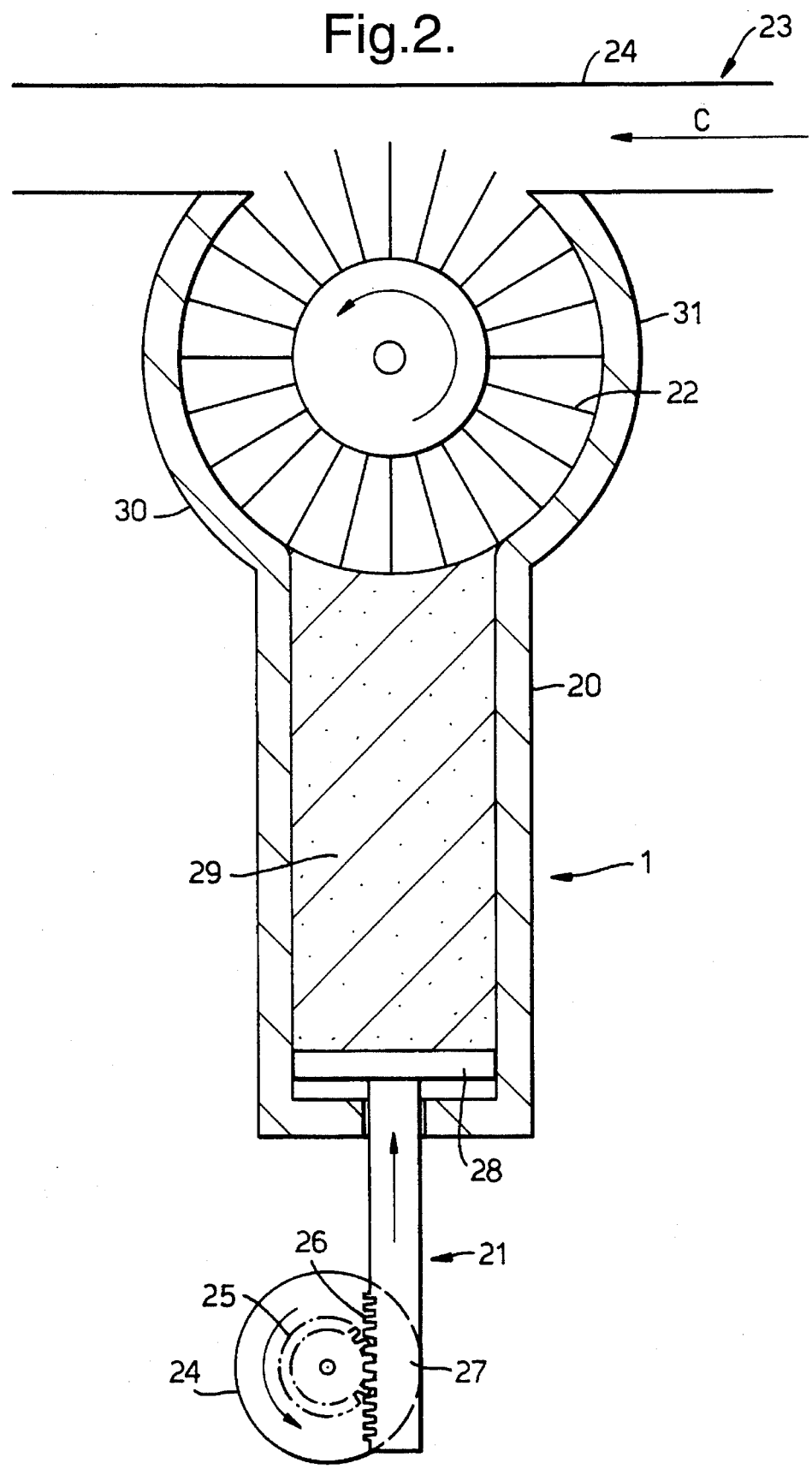

In order that the invention may be clearly understood and readily carried into effect, reference will now be made, by way of example, to the accompanying diagrammatic drawings, in which:

FIG. 1 shows an apparatus operable to calibrate particle emission-detecting instruments; and FIG. 2 shows in vertical cross-section, a material supply device of the apparatus of FIG. 1.

The apparatus shown in FIG. 1 comprises a supply device, generally designated by reference numeral 1, a horizontally extending duct 2 of circular cross-section and mounting means (3a/b), 4 and 5. The supply device 1 communicates with a duct 2 via a conduit 6. Particle emission-detecting instruments are represented by reference numerals 7 and 8. Particle emission-detecting instruments 7 and 8 are held in position at the duct 2 by the mounting means (3a/b) and 4 respectively. Various types of instruments are suitable for detecting particle emissions and the skilled person will know which type of emission-detecting instrument is appropriate for any given situation. In this particular embodiment of the invention, 7 represents an opacity monitor and 8 represents a particle impingement system. The opacity monitor 7 takes measurements across the cross-section of the duct 2 and sub-units thereof are therefore mounted in opposition across the duct 2 by the mounting means 3a and 3b.

The direction of flow of particulate material, from device 1, in conduit 6 and to the duct 2 is represented by an arrow A. A gas stream flows within the duct 2 in a direction represented as by arrow B.

As can be seen from FIG. 2, the supply device 1 includes a vertically extending material containment chamber 20 of circular cross-section, material feed means generally designated by reference numeral 21, a rotary brush 22, which provides transfer means, and entrainment means 23. The material feed means 21 comprises an electronic stepping motor 24. Mounted on the spindle of the motor 24 is a drive gear 25 which meshes with teeth 26 of a vertically extending rod 27. Unitary with the rod 27, at the upper end thereof, is a piston 28, which piston is slidably located within the chamber 20. The rotary brush 22 is driven by drive means (not shown) in the direction indicated by the arrow thereon. The brush 22 is located such that the outer end of the bristles thereof are just in contact with the upper surface of a body of particulate material 29 in chamber 20. Furthermore, the periphery of the brush 22 is bounded by containment walls 30,31. The entrainment means 23 comprises a duct 24 through which there flows a gas stream. The direction of flow of the gas stream of the entrainment means 23 is indicated by arrow C. The gas flow of the entrainment means originates from a controllable, constant compressed gas supply (not shown). As may be seen from FIG. 2, an upper portion of the brush 22 projects into the duct 24.

In operation of the apparatus of FIGS. 1 and 2, the electronic stepper motor 24 drives the drive gear 25 in the direction shown by the arrow. Interaction between the drive gear 25 and the teeth 26 effects an upward movement of the piston 28. The body of particulate material 29 is thereby moved in an upward direction towards the rotary brush 22. The rotary brush 22 carries particulate material from the upper surface of the body of particulate material 29 to the entrainment means 23. The gas stream of the entrainment means 23 serves to remove particulate material from the upper portion of the rotary brush 22 and to carry the particulate material into and through the conduit 6. Upon exiting the conduit 6, the particulate matter entrained in the gas stream of the entrainment means is dispersed into the duct 2 in the overall gas flow therein. As can be seen from FIG. 1, the particle emission-detecting instruments 7 and 8 are positioned at the duct 2 downstream of the point of introduction of the particulate matter into the duct 2. The particle emission-detecting instruments 7 and 8 detect the particulate matter introduced upstream thereof. The readings given by the particle emission-detecting instruments are compared with the accurately known amount of particulate matter introduced into the duct 2 by means of the supply device 1 and the entrainment means 23. The instruments 7 and 8 are then calibrated to read accordingly.

The supply device is capable of introducing amounts of particulate matter into a gas stream in the duct at levels as low as about 0.1 $mg.s^{-1}$. The concentration of particulate matter in the duct will depend upon the feed rate of the supply device and the gas flow rate in the duct. Lower concentrations of particulate matter can be achieved by increasing the gas flow rate in the duct for a given particulate matter feed rate.

The amount of material fed into the duct can be altered at specific stages of the testing period, to enable the particle emission-detecting instruments to be calibrated at various levels of particle emission. This will enable a calibration curve to be produced showing the variation of the particulate emission-detecting instrument reading with the amount of particulate material fed into the duct. In comparison, the method of BS3405 will produce only a single calibration reading for any given situation.

An advantage of apparatus such as that above described is the higher degree of accuracy to which emission-detecting instruments can be calibrated. In accordance with the present invention the feed of particulate matter into the duct can be controlled to within ±2%.

Advantageously, the supply device may be apparatus as disclosed in U.S. Pat. No. 4,764,057 (Mölter et al). A suitable supply device is the Palas Powder Dispersion Generator Model RBG-1000, which is supplied, in the U.K., by the Bristol Industrial and Research Association Limited (BIRAL), Bristol, England, it being manufactured by Palas GmbH, Carlsruhe, Germany.

A further advantage appertaining to the present invention is that particle emission-detecting instruments can be calibrated at very low levels of particle emission. The current methods of calibrating particle emission-detecting instruments, according to the method of BS 3405, do not give accurate, consistent results at very low levels of particle emission.

I claim:

1. A method of calibrating a particle emission-detecting instrument, wherein particulate material is introduced at a controlled rate into a gas stream flowing through a duct, and during the controlled rate introduction of said particulate material into said gas stream said instrument is caused to provide a detection value of the concentration of said particulate material within said gas stream in said duct, whereby said instrument is calibrated.

2. A method in accordance with claim 1, wherein said particulate material is a dust-like material.

3. A method in accordance with claim 2, wherein said dust-like material is exemplary of that monitored by said particle emission-detecting instrument.

4. A method of calibrating a particle emission-detecting instrument, wherein the particulate material is introduced at a controlled rate into a gas stream flowing through a duct, the introduction being by means of a supply device, the supply device comprising a material containment chamber, material feed means, transfer means and entrainment means, said feed means being operable to feed a body of said particulate material contained in said chamber towards said transfer means, said transfer means being operable to transfer said particulate material from the upper surface of said body of particulate material to said entrainment means, and said entrainment means being operable to entrain said particulate material into said gas stream from said transfer means, wherein during the controlled rate introduction of said particulate material into said gas stream, said instrument is caused to provide a detection value of the concentration of said particulate material in said gas stream in said duct, whereby said instrument is calibrated.

5. A method in accordance with claim 4, wherein said body of particulate material takes the form of a vertically extending such body.

6. A method in accordance with claim 4, wherein said body of material is fed upwardly by means of an upwardly movable piston of said feed means.

7. A method in accordance with claim 4, wherein particulate material is transferred from said upper surface of said body of particulate material by the rotation of a rotary brush of said transfer means.

* * * * *